(12) United States Patent
Kouno et al.

(10) Patent No.: US 7,641,450 B2
(45) Date of Patent: Jan. 5, 2010

(54) TRANSPORTING METHOD AND TRANSPORTING FACILITY FOR EASILY POLIMERIZABLE MATERIAL

(75) Inventors: Michiyuki Kouno, Hiroshima-ken (JP); Yasuhiro Kabu, Hiroshima-ken (JP); Yoshiyuki Taniguchi, Hiroshima-ken (JP); Nobuo Momodomi, Hiroshima-ken (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 814 days.

(21) Appl. No.: 10/507,695

(22) PCT Filed: Mar. 27, 2003

(86) PCT No.: PCT/JP03/03856

§ 371 (c)(1),
(2), (4) Date: May 23, 2005

(87) PCT Pub. No.: WO03/082790

PCT Pub. Date: Oct. 9, 2003

(65) Prior Publication Data

US 2005/0207904 A1    Sep. 22, 2005

(30) Foreign Application Priority Data

Mar. 28, 2002   (JP) .............................. 2002-092511

(51) Int. Cl.
*F04B 49/03* (2006.01)
*F04B 23/04* (2006.01)

(52) U.S. Cl. .................. 417/62; 417/53; 137/513.3

(58) Field of Classification Search .................. 417/62, 417/426, 216, 286, 430; 137/513.3, 565.33
See application file for complete search history.

(56) References Cited

U.S. PATENT DOCUMENTS 1,338,906 A * 5/1920 Coulson ..................... 417/432

(Continued)

FOREIGN PATENT DOCUMENTS

| EP | 1 092 874 | 4/2001 |
| JP | 8-49684 | 2/1996 |
| JP | 8-73398 | 3/1996 |

OTHER PUBLICATIONS

"Design of Mechanics of Processing Equipment Series 3; Piping", Edited by the Society of Chemical Engineers, Japan, p. 129 and the translation of Figure 6.1 of p. 129, May 20, 1972.

*Primary Examiner*—Charles G Freay
*Assistant Examiner*—Philip Stimpert
(74) *Attorney, Agent, or Firm*—Oblon, Spivak, McClelland, Maier & Neustadt, L.L.P.

(57) ABSTRACT

The present invention aims to provide a transfer method and a transfer facility for an easily polymerizable substance that limits standing retention of the easily polymerizable substance in the feed pump, etc., and the generation and adherence of solid matter such as polymer or precipitate that accompanies such retention, in a facility in which respective feed pumps are disposed at the plurality of passages that branch off at the easily polymerizable substance inflow side and converge at the easily polymerizable substance outflow side. In this easily polymerizable substance transfer method, in the case where one feed pump 13 operates and the other feed pump 14 is stopped, a portion of the easily polymerizable substance is fed to feed pump 14 and second passage 12 in a direction that is opposite to the direction of flow of the easily polymerizable substance when feed pump 14 is activated. In this easily polymerizable substance transfer facility, a check valve 22 provided downstream to feed pump 14 has a hole in the valve plug that permits passage of the easily polymerizable substance.

15 Claims, 5 Drawing Sheets

U.S. PATENT DOCUMENTS

| | | | |
|---|---|---|---|
| 2,883,360 A * | 4/1959 | Coover, Jr. et al. | 525/255 |
| 4,433,701 A * | 2/1984 | Cox et al. | 137/101.19 |
| 6,135,724 A * | 10/2000 | Yoder et al. | 417/286 |
| 6,454,541 B1 * | 9/2002 | Ijiri et al. | 417/53 |
| 2001/0015226 A1 * | 8/2001 | Hamamoto et al. | 137/563 |
| 2002/0008064 A1 * | 1/2002 | Hamamoto et al. | 210/435 |

* cited by examiner

BACKGROUND ART

TRANSPORTING METHOD AND TRANSPORTING FACILITY FOR EASILY POLIMERIZABLE MATERIAL

BACKGROUND OF THE INVENTION

1. Field of the Invention

The present invention relates to a transfer method for an easily polymerizable substance like (meth)acrylic acid, (meth)acrylic ester, (meth)acrolein or the like, as well as for liquids containing such easily polymerizable substances, and to a facility therefore. More specifically, the present invention relates to a transfer method for an easily polymerizable substance and to a transfer facility therefore, which limit standing retention of the easily polymerizable substance in the feed pump, etc. inside the facility, and the generation of polymers that accompany such retention.

Priority is claimed on Japanese Patent Application No. 2002-92511, filed Mar. 28, 2002, the content of which is incorporated herein by reference.

2. Description of Related Art

Such easily polymerizable substances as (meth)acrylic acid, (meth)acrylic ester and (meth)acrolein undergo polymerization extremely readily. When manufacturing or handling these substances, polymerized substances arise from these and, in some cases, necessitate stoppage of the device or process.

When manufacturing (meth)acrylic acid, (meth)acrylic ester and (meth)acrolein, conventionally known countermeasures to the aforementioned problem include: i) adding a polymerization inhibitor such as hydroquinone, phenothiazine, etc.; and, further, ii) performing a surface polishing treatment inside the device in order to prevent adherence of solid matter such as polymer material or precipitate to the inside of the device; iii) cooling (or, in some cases, heating) the device from the outside; and iv) preventing stay of fluid or retention. However, the conventional technology has yet to be successful in fully preventing the generation or adherence of solid matter like polymer or precipitate material When transferring an easily polymerizable substance such as (meth)acrylic acid, (meth)acrylic ester or (meth)acrolein, a feed pump disposed along the transfer passage is typically employed. An emergency or a back-up feed pump, provided in case of malfunction of the main feed pump, and an auxiliary feed pump, for temporarily increasing transfer capacity, (the term "reserve feed pump" being employed hereinafter for both), are provided in parallel to the aforementioned main feed pump. So that they begin operating immediately in the event of an emergency, at least one of reserve feed pumps is always connected to the transfer passage and is filled with the easily polymerizable substance.

Figure 7:
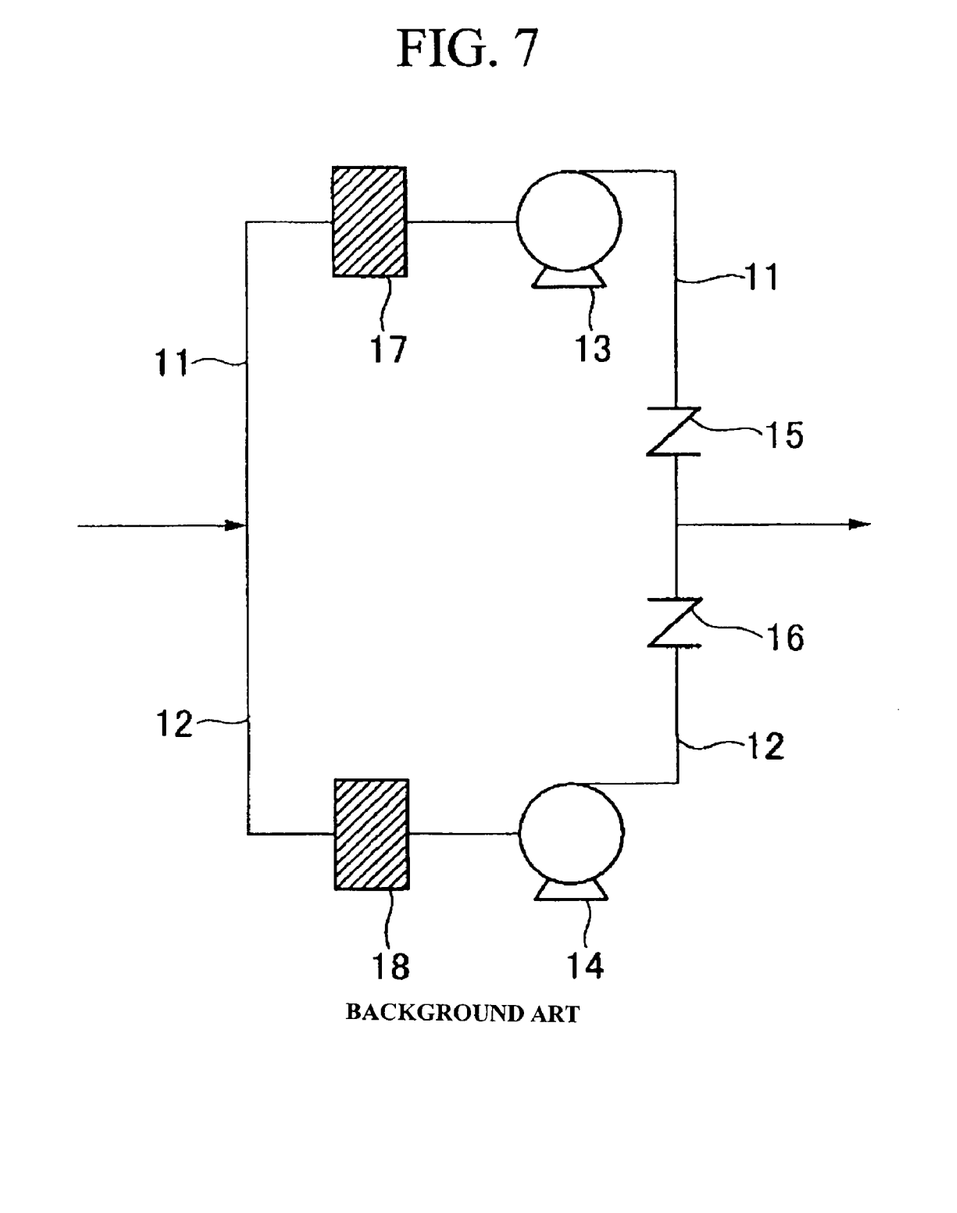
FIG. 7 is a schematic structural view showing an example of a conventional transfer facility for an easily polymerizable substance.

FIG. 7 is a schematic structural diagram showing an example of a transfer facility for an easily polymerizable substance in which the two feed pumps are disposed in parallel. Feed pumps 13 and 14 are respectively provided to a first passage 11 and a second passage 12 which branch off from each other at the easily polymerizable substance inflow side, and converge at the easily polymerizable substance outflow side in the transfer facility. Respective check valves 15 and 16 are provided at positions downstream to feed pumps 13 and 14, so that when one of either feed pumps 13 and 14 is stopped, the easily polymerizable substance does not flow from the outflow to the inflow side through the passage of the halted feed pump, or does not flow backward. In addition, strainers 17 and 18 for removing foreign material are provided at a position upstream from feed pumps 13 and 14.

However, in an easily polymerizable substance transfer facility of this type, in which at least one of emergency and at least one of auxiliary feed pumps are provided, the easily polymerizable substance is retained in the reserve feed pump, which is held in the halted stated, and in its strainer and the passage for the pump and the strainer. As a result, generation of solid matter such as polymer, becomes a problem. When such polymer material is generated, it becomes impossible to use the easily polymerizable substance transfer facility, and operational anomalies occur as a result of the polymer material.

In addition, when it becomes necessary to immediately switch to the reserve feed pump in the case where transferring a high-temperature (at least 40° C., for example) easily polymerizable substance, it is possible for heat shock to occur at the moment the high-temperature easily polymerizable substance is introduced into the passage for the reserve feed pump due to the temperature difference between the easily polymerizable substance and the cooler pipes. As a result of this heat shock, leakage of the easily polymerizable substance from the connections between pipes may occur, leading in some cases to damage of the facility.

SUMMARY OF THE INVENTION

It is therefore an objective of the present invention to provide a transfer method and a transfer facility for an easily polymerizable substance that limits standing retention of the easily polymerizable substance in the feed pump, etc., and the generation and adherence of solid matter such as polymer or precipitate that accompanies such retention, in a facility in which feed pumps are respectively disposed at the plurality of passages that branch off at the easily polymerizable substance inflow side and converge at the easily polymerizable substance outflow side.

In other words, the transfer method of the present invention for an easily polymerizable substance is a method for transferring an easily polymerizable substance using feed pumps that are respectively disposed at a plurality of passages that branch off at the easily polymerizable substance inflow side and converge at the easily polymerizable substance outflow side, wherein, when at least one of the feed pumps is stopped, some of the easily polymerizable substance is fed to the stopped feed pump and to the passage disposed thereat in a direction that is opposite to the direction of flow of the easily polymerizable substance when the at least one feed pump is activated.

The present invention is particularly effective in the case where the easily polymerizable substance to be transferred includes at least one selected from (meth)acrylic acid, (meth)acrylic ester and (meth)acrolein.

The present invention is particularly effective in the case where the easily polymerizable substance to be transferred is heated to at least 40° C.

The present transfer facility of the present invention for an easily polymerizable substance is a transfer facility for an easily polymerizable substance in which feed pumps and check valves downstream thereof are respectively disposed at a plurality of passages that branch off at the easily polymerizable substance inflow side and converge at the easily polymerizable substance outflow side, wherein each check valve has a hole in the valve plug that permits passage of the easily polymerizable substance.

In addition, the present invention is particularly effective in the case where at least one of feed pumps is a main pump that operates at all times, while at least one of others is a emergency pump which is operable in place of at least one of the main pumps when at least one of the main pumps stops, or is an auxiliary pump for temporarily increasing transfer volume.

It is preferable that the check valve be a swing-type check valve.

It is preferable that the diameter of the hole formed in the valve plug of the check valve be 0.1 to 20% of the outer diameter of the valve plug.

DETAILED DESCRIPTION OF THE INVENTION

The present transfer facility of the present invention for an easily polymerizable substance is a facility that is equipped with a feed pump for transferring the easily polymerizable substance. Specifically, the present transfer facility of the present invention for an easily polymerizable substance is a facility in which feed pumps are respectively disposed at a plurality of passages that branch off at the easily polymerizable substance inflow side and converge at the easily polymerizable substance outflow side, this facility having a main feed pump that operates at all times and a reserve feed pump that is immediately switched to during an emergency, and check valves that are disposed downstream from at least one of the feed pumps for preventing reverse flow.

Provided that it is a substance that readily polymerizes, the easily polymerizable substance in the present invention is not particularly restricted. Polymerizable vinyl compounds may be cited, for example. Examples of polymerizable vinyl compounds include unsaturated carbonic acids such as (meth) acrylic acid; alkyl (meth)acrylates such as methyl (meth) acrylate, normal butyl (meth)acrylate, isobutyl (meth) acrylate, tertiary butyl (meth)acrylate, 2-ethylhexyl (meth) acrylate, lauryl (meth)acrylate, tridecyl (meth)acrylate, and stearyl (meth)acrylate; (meth)acrylates containing alicyclic, aromatic, heterocyclic and vinyl groups, such as cyclohexyl (meth)acrylate, benzyl (meth)acrylate, isobornyl (meth)acrylate, glycidyl (meth)acrylate, tetrahydrofurfuryl (meth)acrylate, and aryl (meth)acrylate; (meth)acrylates containing hydroxyl or alkoxyl groups such as hydroxyethyl (meth)acrylate, hydroxypropyl (meth)acrylate, 2-methoxyethyl (meth) acrylate, and 2-ethoxyethyl (meth)acrylate; multifunctional (meth)acrylates such as ethylene glycol di(meth)acrylate, triethylene glycol di(meth)acrylate, 1,3-butylene glycol di(meth)acrylate, 1,6-hexanediol di(meth)acrylate, polypropylene glycol di(meth)acrylate, and trimethylolpropane tri (meth)acryalte; (meth)acrylates containing carbonic acid such as 2-(meth)acryloloxyethyl phthalate, 2-(meth)acryloloxyethyl hexahydrophthalate; dialkylaminoethyl (meth) acrylates such as dimethylaminoethyl (meth)acrylate, dimethylaminoethyl (meth)acrylate methylchloride, dimethylaminoethyl (meth)acrylate benzyl chloride, and diethylaminoethyl (meth)acrylate; halogenated alkyl (meth) acrylates such as trifluoroethyl (meth)acrylate or heptadecafluorodecyl (meth)acrylate; and unsaturated aldehydes such as (meth)acrolein. The easily polymerizable substance may be a single substance or a mixture of a plurality of compounds.

As used here, the term "(meth)acrylic acid" means acrylic acid or methacrylic acid, the term "(meth)acrylate" means acrylate or methacrylate, and the term "(meth)acrolein" means acrolein or methacrolein.

The easily polymerizable substance in the present invention also includes liquids that contain an aforementioned easily polymerizable substance. An example of a liquid including an easily polymerizable substance is a mixture of an aforementioned easily polymerizable substance and a byproduct or an unreacted material from the generation or synthesis of the easily polymerizable substance, or a liquid in which is mixed a third component solvent that is unreactive with respect to the easily polymerizable substance, such as water, toluene, hexane or the like.

The present transfer facility of the present invention for an easily polymerizable substance will now be explained in detail with reference to the figures.

Figure 1:
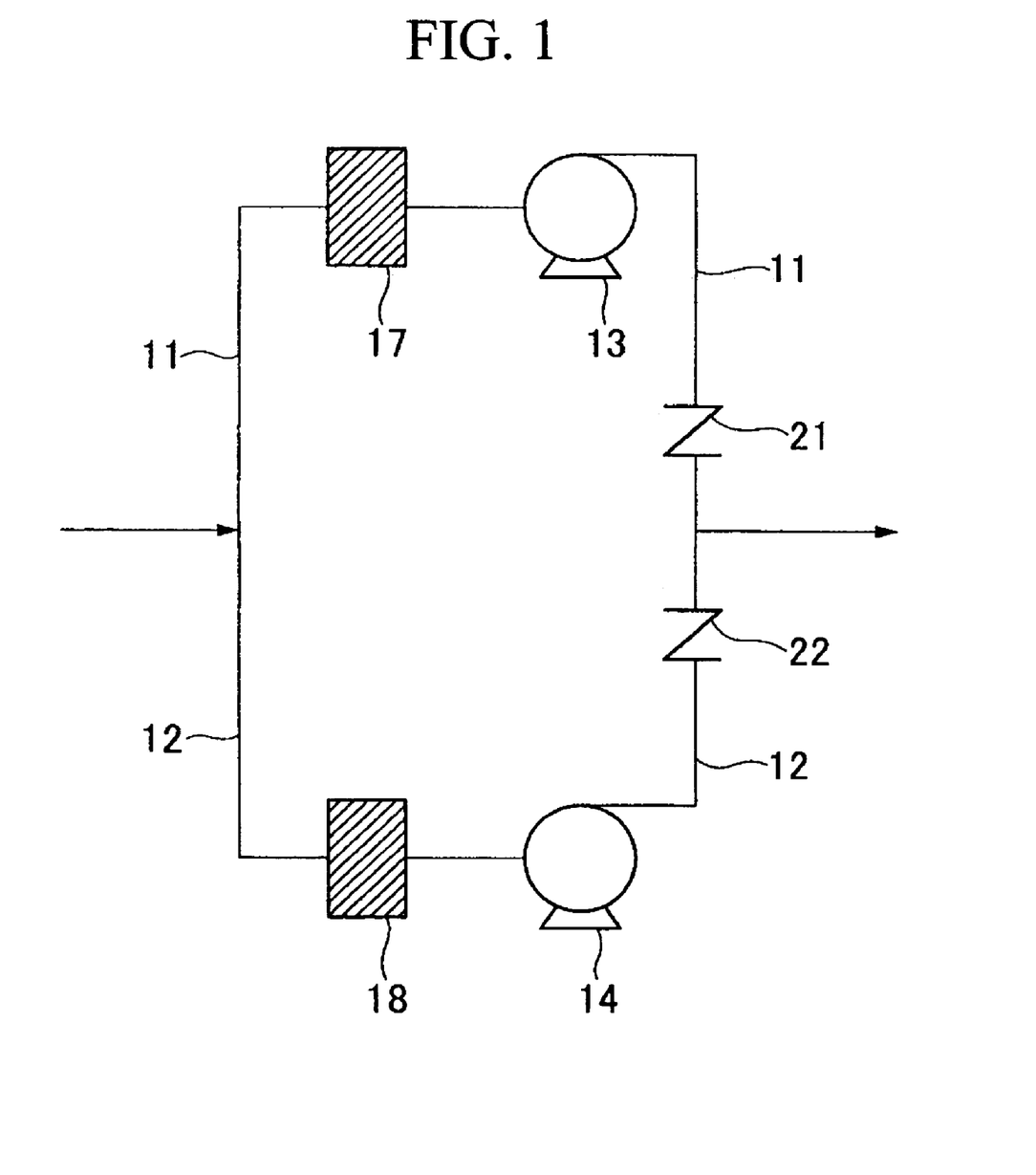
FIG. 1 is a schematic structural view showing an example of the present transfer facility of the present invention for an easily polymerizable substance.

FIG. 1 is a schematic structural view showing one example of the present transfer facility of the present invention for an easily polymerizable substance. In this transfer facility, feed pumps 13 and 14 are respectively disposed at a first passage 11 and a second passage 12 that branch off at the easily polymerizable substance inflow side and converge at the easily polymerizable substance outflow side. Respective check valves 21 and 22 are provided downstream to feed pumps 13 and 14, and respective strainers 17 and 18 for removing foreign material are provided upstream to feed pumps 13 and 14.

Figure 2:
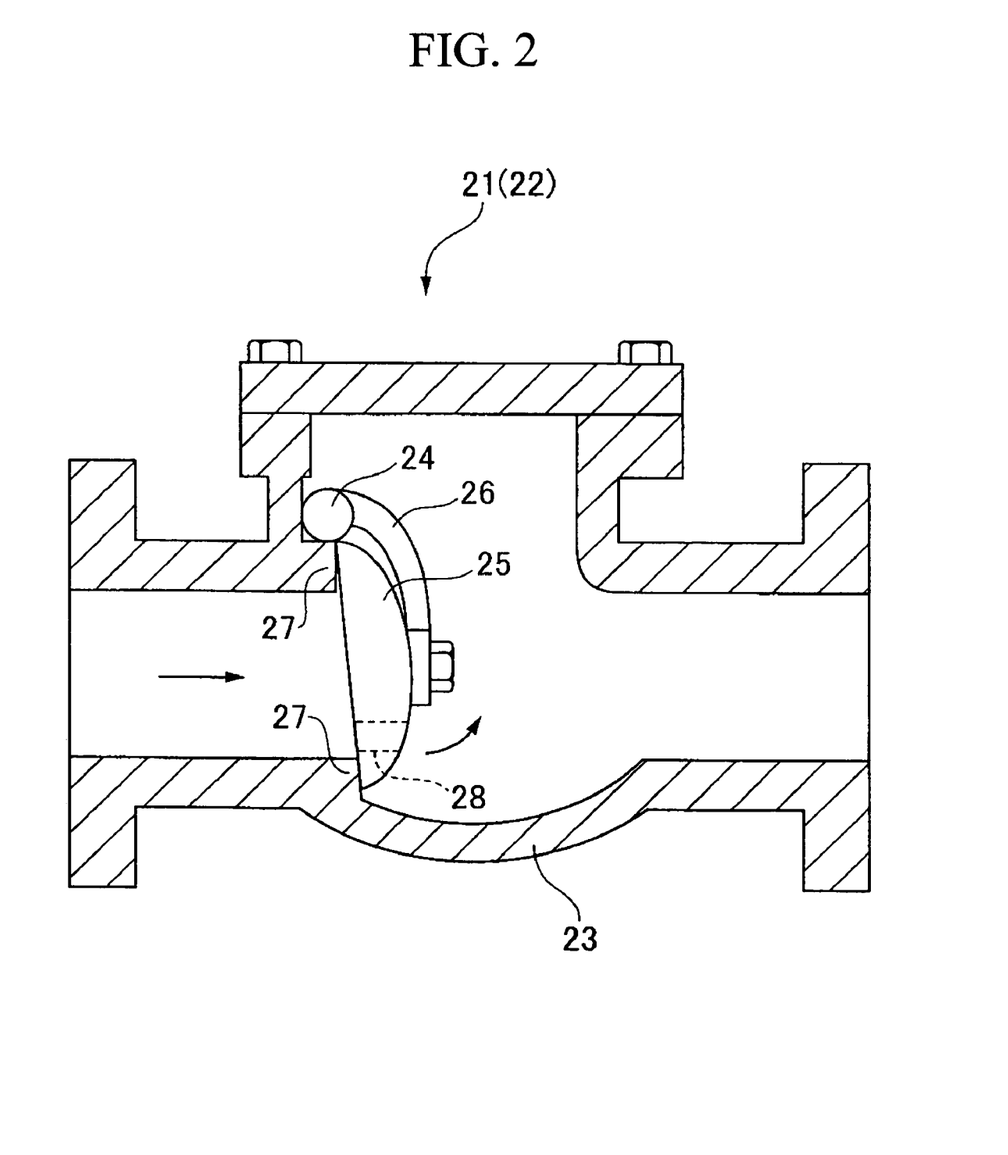
FIG. 2 is a cross-sectional view showing an example of the check valve in the present transfer facility of the present invention for an easily polymerizable substance.

As shown in FIG. 2, disc-shaped valve plug 25 of check valve 21(22) is supported by a bearing axis 24, which is provided inside valve casing 23, so as to permit swinging motion of valve plug 25 via arm 26. Check valve 21(22) is a swing-type check valve in which valve plug 25 contact and move away from valve seat 27, which surrounds the inflow passage formed inside valve casing 23. When transferring an easily polymerizable substance, valve plug 25 is disposed at the passage so as to move away from valve seat 27. Further, as shown in FIGS. 3 and 4, a small diameter throughhole 28 is made in valve plug 25 of check valve 21 in a manner so as to avoid the area of contact between valve plug 25 and valve seat 27, and arm 26.

Figure 3:
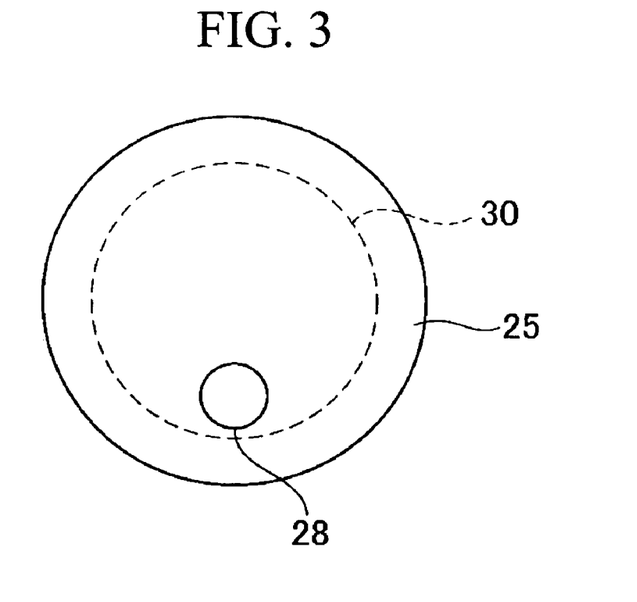
FIG. 3 is a view of the valve plug of the check valve in FIG. 2 as seen from the insertion side of the check valve.
Figure 4:
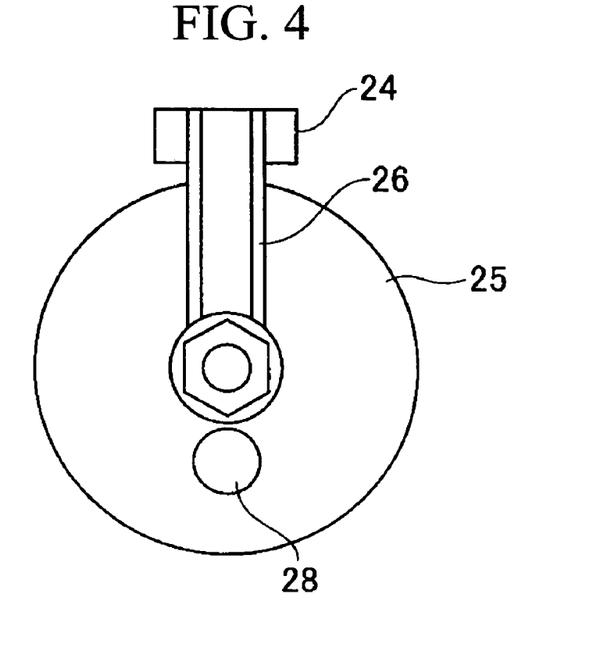
FIG. 4 is a view of the valve plug of the check valve in FIG. 2 as seen from the exit side of the check valve.

Dashed line 30 in FIG. 3 indicates the boundary between the area where valve plug 25 and valve seat 27 contact and the area where valve plug 25 and valve seat 27 do not contact.

The position at which throughhole 28 is made is not particularly restricted.

However, so that a small amount of the easily polymerizable substance flows through check valve 21 even when the feed pump is stopped and the passage is closed off by valve plug 25, it is preferable to position throughhole 28 where it will not be blocked off, for example, it is preferable to position throughhole 28 so that it avoids the area of contact between valve plug 25 and valve seat 27, the area at which arm 26 is fixed, and area covered by arm 26.

Figure 5:
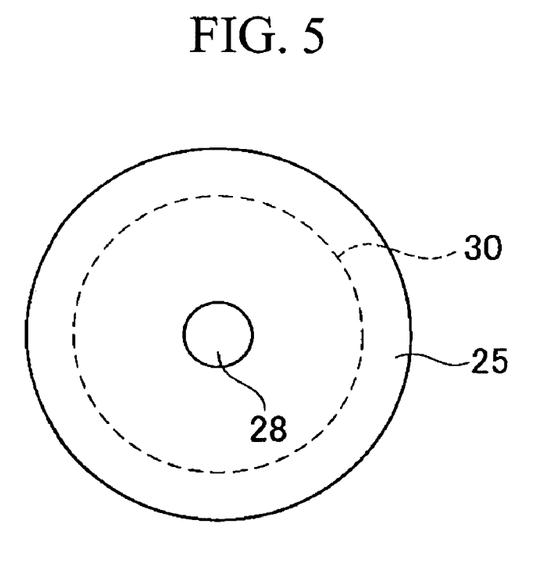
FIG. 5 is a view showing another example of the valve plug of the check valve in the present transfer facility of the present invention for an easily polymerizable substance, as seen from the insertion side of the check valve.
Figure 6:
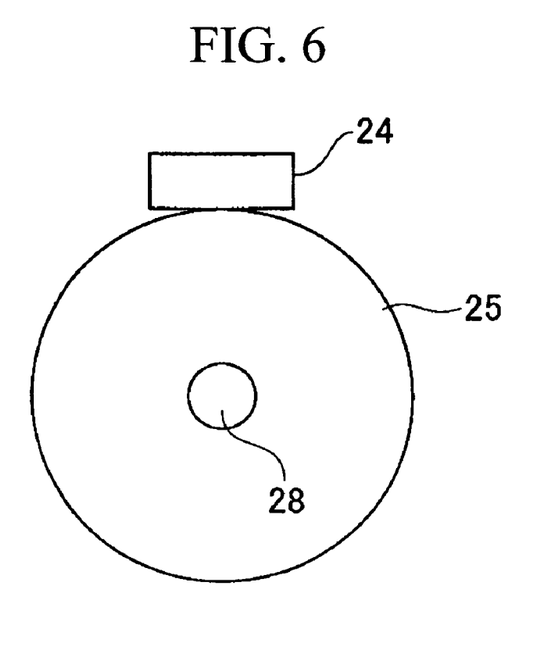
FIG. 6 is a view showing another example of the valve plug of the check valve in the present transfer facility of the present invention for an easily polymerizable substance, as seen from the exit side of the check valve.

When an arm is not attached to valve plug 25, then throughhole 28 may be made in the center of valve plug 25, as shown in FIGS. 5 and 6.

The diameter of throughhole 28 is not particularly restricted, with any dimension being acceptable provided that the amount of flow resulting does not have a negative impact on the feed pump, even when the easily polymerizable substance flows backward via throughhole 28. The diameter of throughhole 28 is preferably 0.1 to 20% of the outer diameter of valve plug 25. When the diameter of throughhole 28 is less than 0.1% of the outer diameter of valve plug 25, the flow volume of the easily polymerizable substance flowing through throughhole 28 is too small, giving rise to the possibility of standing retention of the easily polymerizable substance in the reserve feed pump in stopped state, strainer or the passage where these are located. On the other hand, when the diameter of throughhole 28 is greater than 20% of the outer diameter of valve plug 25, the essential function of the check valve is impaired.

In general, the ratio of the outer diameter of valve plug 25 with respect to the diameter of the area in which valve plug 25 does not contact valve seat 27 becomes smaller as the size of the check valve becomes larger. Accordingly, in the present invention, the limits for the diameter of throughhole 28 are prescribed in terms of a proportion with respect to the outer diameter of valve plug 25. However, strictly speaking, the diameter of throughhole 28 must be set so that it does not impair the function of the check valve, and after taking into consideration the negative impact of backward flow on the feed pump.

A pump that is typically employed to transfer fluid may be employed as feed pump 13(14), and is not restricted in particular. Examples of this type of feed pump that may be cited include a centrifugal pump, propeller pump, and the like.

Strainer 17(18) is also not particularly restricted, as long as it is capable of removing foreign matter, such as solid material that is included in the easily polymerizable substance.

Next, the transfer of an easily polymerizable substance that employs the easily polymerizable substance transfer facility shown in the figures will be explained.

First, the operation of feed pump 13 is initiated, and an easily polymerizable substance is moved along first passage 11 from the inflow side toward the outflow side. Feed pump 14 is in the stopped state at this time.

The easily polymerizable substance flowing from the inflow side flows through first passage 11, sequentially passing through strainer 17, feed pump 13, and check valve 21, and passes to the outside of the facility on the outflow side. Due to the presence of throughhole 28, which has been provided in the valve plug 25 of the check valve 22 for second passage 12, a portion of the easily polymerizable substance that has flown along first passage 11 to the outflow side, flows from the area of confluent flow from first passage 11 and second passage 12, into the second passage. In other words, with valve plug 25 in the closed state, a portion of the easily polymerizable substance passes through throughhole 28 of check valve 22, and flows backward through check valve 22, feed pump 14 and strainer 18 sequentially, to finally flow from the first passage 11 and second passage 12 branch point, into first passage 11, commingling with the flow there.

Thus, most of the easily polymerizable substance that flows from the inflow side in this way into the easily polymerizable substance transfer facility exemplified in the figures, is sent through first passage 11 by feed pump 13, the main pump to the outside of the facility trough outflow side. However, a portion of this easily polymerizable substance also circulates between feed pump 13 and reserve feed pump 14, which are disposed in parallel, due to the pressure of feed pump 13.

In the above described transfer facility for an easily polymerizable substance, a throughhole 28 is provided in valve plug 25 of check valve 22. As a result, even if reserve feed pump 14 is stopped, a portion of the easily polymerizable substance flows backward to second passage 12 due to the pressure of feed pump 13 which is operating.

Accordingly, when transferring an easily polymerizable substance using this type of easily polymerizable substance transfer facility, there is no standing retention of the easily polymerizable substance in strainer 18, feed pump 14, check valve 22, or second passage 12 along which these are disposed, even if reserve feed pump 14 is stopped. As a result, the generation and adherence of solid matter such as polymer or precipitate in the easily polymerizable substance transfer facility is controlled.

Further, in this easily polymerizable substance transfer facility, the reserve feed pump 14 is always connected to a passage. As a result, it is always full of the easily polymerizable substance and therefore immediately begin operation when main feed pump 13 suffers a malfunction, etc.

In this easily polymerizable substance transfer facility, a portion of the easily polymerizable substance is always flowing through second passage 12. Thus, when transferring a high temperature easily polymerizable substance, even in the case where it is suddenly necessary to employ reserve feed pump 14, there is almost no temperature difference between the easily polymerizable substance and the piping of the second passage 12. Thus, there is no predisposition to damage to the facility or leaking of the easily polymerizable substance at the piping connections from heat shock.

It should be noted that the present transfer facility of the present invention for an easily polymerizable substance is not restricted to the examples shown in the figures. For example, a facility with at least three feed pumps disposed in parallel is also acceptable.

In addition, it is also acceptable to provide temperature adjusting equipment as needed to the present transfer facility of the present invention for the easily polymerizable substance. For example, in the case where the easily polymerizable substance to be transferred is a substance having a high temperature of solidification, such as (meth)acrylic acid, and the temperature inside and outside the facility is near, equal or below the solidification temperature so that there is a chance that the easily polymerizable substance may solidify at low flow volumes, then it is acceptable to provide a heating device to the piping, valves, check valves, etc. Conversely, when the temperature inside and outside the facility is a temperature or condition that may invite polymerization of the easily polymerizable substance, then it is acceptable to provide a cooling device to the piping, valves, check valves, etc.

Further, the check valve is not restricted to the swing-type valve exemplified in the figures. Rather, conventionally known check valves such as swing-type or lift-type check valves may be employed. However, from the perspective of the ease of creating a hole in the valve plug, a swing-type check valve is optimally employed as a check valve.

By including a polymerization inhibitor in a liquid that contains an easily polymerizable substance, it is possible to even further improve the polymerization inhibiting effect. Examples of polymerization inhibitors include hydroquinone, phenothiazine, methoquinone, manganese acetate, nitrosophenol, cupferron, N-oxyl compounds and the like.

EXAMPLES

The present invention will now be further explained, using the examples that follow below. However it should be noted that the present invention is in no way limited thereto.

Example 1

Using the transfer facility for easily polymerizable substances shown in FIG. 1, methacrolein was supplied from a storage tank (not shown in the figures) to a distillation process.

To maintain the temperature of the storage tank at not more than −10° C., a cooling medium was employed and cooling of the storage tank was performed using a jacket and an internal coil. A small diameter piping was wrapped around first passage 11 and second passage 12, which are the methacrolein supply pipes, valves (not shown), check valves 21, 22, etc., which were installed the storage tank, and the cooling medium was passed through the small diameter piping around the outside of these parts, cooling them. Feed pump 13 was employed as the main pump, and feed pump 14 was the reserve feed pump which is immediately switched to for use in case of malfunction of the main pump. Centrifugal pumps of equivalent capacity were employed for feed pumps 13 and 14.

Throughhole 28, having a diameter that was 10% of the outer diameter of valve plug 25, was provided in valve plug 25 inside check valves 21 and 22. A valve having the valve plug shown in FIGS. 5 and 6 was employed for the check valves, and throughhole 28 was formed in the middle of valve plug 25.

The distillation process, which was the next step, is a process in which the methacrolein is distilled and purified in a distillation tower that is equipped with an evaporative shell and tube type heat exchanger.

When executing the supply of methacrolein from the storage tank to the distillation process using this easily polymerizable substance transfer facility, stoppage of the supply pump due to malfunction, poor opening or closing of the valve, and clogging of the piping of the first passage 11, second passage 12 due to the occurrence of polymerization, did not occur at all, even in the case where switching from main pump to the reserve feed pump.

In addition, there were no polymerization problems inside the heat exchanger during the distillation process prior to supply of the easily polymerizable substance.

Comparative Example 1

With the exception that a throughhole was not provided in the valve body of the check valve, the supply of methacrolein from the storage tank to the distillation process was carried out in the same manner as in Example 1.

The reserve feed pump (feed pump 14) which is stopped and second passage 12 along which this pump is disposed were filled with methacrolein and held in this state. As a result, polymerization of the methacrolein inside the piping of second passage 12 occurred as a result of standing retention of the methacrolein. Immediately after switching from the main pump to the reserve pump, clogging of strainer 18 disposed upstream from feed pump 14, and stoppage of the pump due to malfunction from adherence of polymer inside feed pump 14 occurred with great frequency.

The polymer present inside the supply piping was sent to the distillation process, the next step, and blockage due to polymer in the tube inside the evaporative shell and tube type heat exchanger and poor heat exchange occurred. As a result, emergency stoppage of the process could not be avoided. Malfunctions occurred as frequently as each changeover; specifically, malfunction occurred on the occasion of once pump switchover per every 2 to 3 months, and 3 to 4 malfunctions, such as clogging and the like, occurred with each switchover.

As explained above, the transfer method of the present invention for an easily polymerizable substance is a method for transferring an easily polymerizable substance using feed pumps that are respectively disposed at a plurality of passages that branch off at the easily polymerizable substance inflow side and converge at the easily polymerizable substance outflow side, when at least one of the feed pumps is stopped, wherein some of the easily polymerizable substance is fed to the stopped feed pump and to the passage disposed thereat in a direction that is opposite to the direction of flow of the easily polymerizable substance when the at least one feed pump is activated. As a result, standing retention of the easily polymerizable substance inside a feed pump that is intermittently employed does not occur, even in the case where at least two feed pumps disposed in parallel are used in a switching method or intermittently to transfer the easily polymerizable substance. Thus, it is possible to limit polymerization of the easily polymerizable substance inside the facility.

Further, the present transfer facility of the present invention for an easily polymerizable substance is a transfer facility for an easily polymerizable substance in which feed pumps and check valves downstream thereof are respectively disposed at a plurality of passages that branch off at the easily polymerizable substance inflow side and converge at the easily polymerizable substance outflow side, wherein each check valve has a hole in the valve plug that permits passage of the easily polymerizable substance. Thus, standing retention of the easily polymerizable substance inside the feed pump, and the generation and adherence of solid material such as polymer or precipitate that accompany this is controlled.

In addition, if the check valves are swing-type check valves, then it is effective in terms of costs because of the ease of opening a hole in the valve plug.

Further, if the diameter of the hole that is formed in the valve plug of the check valve has a length that is 0.1 to 20% of the outer diameter of the valve plug, then there is no impairment of the essential function of the check valve, and it is possible to limit standing retention of the easily polymerizable substance inside the facility.

What is claimed is:

1. A transfer method for an easily polymerizable substance in which said easily polymerizable substance is transferred using feed pumps that are respectively disposed at a plurality of passages that branch off at the easily polymerizable substance inflow side and converge at an easily polymerizable substance outflow side, wherein the feed pumps are provided with check valves disposed downstream thereof and before the passages converge at the easily polymerizable substance outflow side, the method comprising:

stopping at least one of the feed pumps; and
while the at least one of the feed pumps is stopped, feeding a portion of the easily polymerizable substance to the at least one stopped feed pump and to the passage disposed thereat in a direction that is opposite to the direction of flow of the easily polymerizable substance provided while the at least one feed pump is activated so that the portion of the easily polymerizable substance passes from a hole in a respective check valve through an outlet of the at least one stopped pump through the pump to an inlet of the at least one stopped pump.

2. The transfer method for an easily polymerizable substance according to claim 1, wherein the easily polymerizable substance to be transferred includes at least one easily polymerizable substance selected from (meth)acrylic acid, (meth) acrylic ester, and (meth)acrolein.

3. The transfer method for an easily polymerizable substance according to claim 2, wherein the easily polymerizable substance to be transferred is heated to at least 40° C.

4. The transfer method for an easily polymerizable substance according to one of claims 1, wherein the easily polymerizable substance to be transferred is heated to at least 40° C.

5. A transfer facility for an easily polymerizable substance, in which feed pumps and check valves downstream thereof are respectively disposed at a plurality of passages that branch off at the easily polymerizable substance inflow side and converge at the easily polymerizable substance outflow side, wherein each said check valve has a hole in a valve plug thereof that permits passage of the easily polymerizable substance, wherein said feed pumps include a first feed pump and a second feed pump, wherein the first feed pump is connected in fluid communication with the second feed pump and the first feed pump is configured to allow fluid to pass from an outlet of the first feed pump through the first feed pump while the first feed pump is stopped.

6. The transfer facility for an easily polymerizable substance according to claim 5, wherein at least one of feed pumps is a main pump that operates at all times, while at least one of other feed pumps is a emergency pump which is operable in place of at least one of the main pumps when at least one of the main pumps stops.

7. The transfer facility for an easily polymerizable substance according to claim 6, wherein each check valve is a swing-type check valve.

8. The transfer facility for an easily polymerizable substance according to claim 6, wherein a diameter of the hole formed in the valve plug of each check valve is 0.1 to 20% of an outer diameter of the valve plug.

9. The transfer facility for an easily polymerizable substance according to claim 5, wherein at least one of feed pump is a main pump that operates at all times, while at least another of the feed pumps is an auxiliary pump for temporarily increasing transfer volume.

10. The transfer facility for an easily polymerizable substance according to claim 9, wherein each check valve is a swing-type check valve.

11. The transfer facility for an easily polymerizable substance according to claim 9, wherein a diameter of the hole formed in the valve plug of each check valve is 0.1 to 20% of an outer diameter of the valve plug.

12. The transfer facility for an easily polymerizable substance according to one of claims 5, wherein each check valve is a swing-type check valve.

13. The transfer facility for an easily polymerizable substance according to one of claims 5, wherein the diameter of the hole formed in the valve plug of each check valve is 0.1 to 20% of the outer diameter of the valve plug.

14. The transfer facility for an easily polymerizable substance according to claim 5, wherein each pump is a centrifugal or propeller pump.

15. The transfer facility for an easily polymerizable substance according to claim 5, wherein strainers are disposed upstream of the feed pumps at the plurality of passages that branch off at the easily polymerizable substance inflow side and converge at the easily polymerizable substance outflow side.

* * * * *